United States Patent [19]

Bosma et al.

[11] Patent Number: 5,713,849
[45] Date of Patent: Feb. 3, 1998

[54] SUCTION CATHETER AND METHOD

[75] Inventors: Gjalt Bosma, Drachten; Alexander Christiaan Boudewijn, Leek, both of Netherlands

[73] Assignee: Cordis Corporation, Miami, Fla.

[21] Appl. No.: 504,203

[22] Filed: Jul. 19, 1995

[51] Int. Cl.[6] .................................. A61M 1/00
[52] U.S. Cl. ...................... 604/28; 604/35; 604/43; 606/159
[58] Field of Search .......................... 604/280–283, 604/284, 264, 246, 35, 16, 7, 28, 43; 606/159

[56] References Cited

U.S. PATENT DOCUMENTS

| 4,637,814 | 1/1987 | Leiboff . | |
|---|---|---|---|
| 4,715,848 | 12/1987 | Beroza | 604/35 |
| 4,781,678 | 11/1988 | De Couet et al. | 604/280 X |
| 4,892,519 | 1/1990 | Songer et al. . | |
| 5,078,688 | 1/1992 | Lobodzinski et al. . | |
| 5,207,648 | 5/1993 | Gross | 604/280 X |
| 5,261,887 | 11/1993 | Walker | 604/264 |
| 5,300,022 | 4/1994 | Klapper et al. | 604/264 X |
| 5,320,599 | 6/1994 | Griep et al. | 604/246 |
| 5,395,352 | 3/1995 | Penny | 604/283 X |
| 5,405,321 | 4/1995 | Reeves | 604/283 X |
| 5,451,233 | 9/1995 | Yock | 604/264 X |
| 5,453,088 | 9/1995 | Boudewijn et al. . | |
| 5,496,267 | 3/1996 | Drasler et al. . | |

FOREIGN PATENT DOCUMENTS

| 0442579 | 8/1991 | European Pat. Off. . |
| 9105575 | 5/1991 | WIPO . |

*Primary Examiner*—Mark Bockelman
*Attorney, Agent, or Firm*—Michael W. Montgomery

[57] ABSTRACT

A suction catheter has a tubular body with a distal end, a proximal end, and an inlet lumen and a discharge lumen formed in the catheter body. At the distal end of the catheter, the inlet lumen is connected with a nozzle, and the discharge lumen opens into a suction inlet. At the proximal end of the catheter, the lumens are connected to a proximal hub having an inlet port and a discharge port. The inlet lumen may be formed in a separate tube received inside the catheter body, and the suction catheter may include a guidewire lumen adapted to receive a guidewire.

13 Claims, 3 Drawing Sheets

SUCTION CATHETER AND METHOD

BACKGROUND AND DESCRIPTION OF THE INVENTION

The present invention relates generally to medical catheters, and more specifically to a suction catheter for removing a substance from a body vessel of a patient.

Suction catheters are designed to remove various substances, including thrombus, from selected areas within the various body vessels, including blood vessels. These catheters are generally constructed with an influent lumen and an effluent lumen within an elongated catheter body. Near the distal tip of the catheter body, an opening in the lateral wall of the catheter body defines a suction inlet which is coupled with the effluent lumen to direct flow from the body vessel into the effluent lumen in a proximal direction to remove the desired substance from the vessel. Outside of the body of the patient, the effluent lumen is coupled with a storage container for holding the removed substances and fluids. The influent lumen is coupled with a nozzle which may be directed in the proximal direction, across the suction inlet and toward the effluent lumen. The proximal end of the influent lumen is connected to a source of pressurized fluid, such as a liquid pump supplied by a liquid reservoir. The pump forces fluid in a generally distal direction through the influent lumen and out of the nozzle, thereby causing a suction force at the suction inlet which tends to draw body fluids and the desired substances into the suction inlet and the effluent lumen.

Suction catheters are described in the commonly assigned patent application Ser. No. 08/227,361, filed on Apr. 13, 1994 and entitled "Hydrodynamic Suction Catheter" by Boudewijn, et al., now U.S. Pat. No. 5,453,088 the disclosure of which is incorporated herein by reference.

It would be desirable to provide a suction catheter which can be used in conjuction with a guidewire, so that the catheter may be more precisely guided through the body vessels.

It would be further desirable to provide a suction catheter having improved longitudinal bending resistance, such that the catheter body tends not to bend when the pressurized fluid is flowing through the influent lumen.

The suction catheter of the present invention may be provided with an additional lumen for accepting a guidewire. This novel configuration may include a distal opening at the distal end of the guidewire lumen, so that the guidewire tip can extend distally beyond the catheter to steer the catheter into the desired body vessel. In addition, the proximal end of the guidewire lumen may be provided with a hemostatic valve for preventing body fluids from escaping the guidewire lumen.

The unique arrangement of the present invention may also include a separate influent tubular member, or pressure tube. This separate tube lies substantially freely inside the lumen of the basic body and does not influence the bending characteristics of the catheter, with its proximal and distal ends sealed to the catheter. When the pressurized fluid flows through the pressure tube, the major portion of the pressure tube is free to adjust slightly in the radial direction. As a result, the bending characteristics of the catheter are only defined by the basic catheter body. Consequently, the catheter according to the present invention has a substantially constant bending stiffness in all radial directions, which is conducive to the prevention of longitudinal bending.

The various objects, advantages and features of the invention will become apparent from the following description and claims, when considered in conjunction with the attached drawings.

DETAILED DESCRIPTION OF THE PREFERRED EMBODIMENTS

The following description of the preferred embodiments of the present invention is merely illustrative in nature, and as such it does not limit in any way the present invention, its application, or uses. Numerous modifications may be made by those skilled in the art without departing from the true spirit and scope of the invention.

Figure 1:
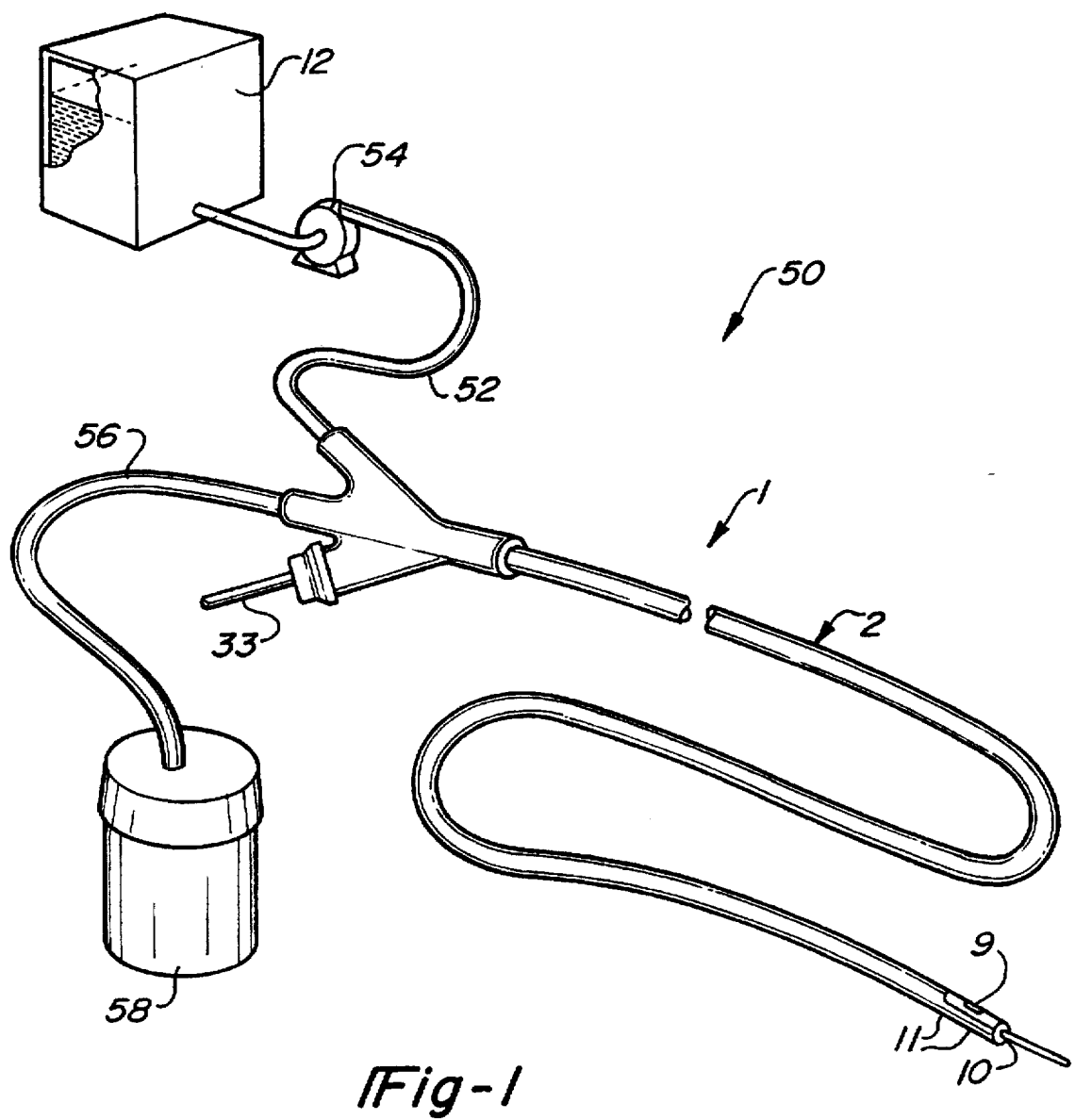
FIG. 1 is a diagrammatic view of a suction catheter system arranged according to the principles of the present invention.

With reference to the drawings, in which identical reference numbers refer to corresponding parts in the various drawing Figures, the suction catheter of the present invention is generally designated by reference numeral 1. FIG. 1 shows the catheter 1 of the present invention in use with a suction catheter system 50, which may include for example an exterior inlet tube 52 and coupled with a source of pressurized fluid, in this case a liquid pump 54 drawing from a fluid reservoir 12, preferably containing liquid. The suction catheter system 50 further includes an exterior discharge tube 56 leading to a discharge reservoir 58.

In addition, the guidewire lumen may also be formed as a separate tube received within the catheter body lumen. Accordingly, the total available cross-section of the catheter body lumen is used most effectively. Even with small diameters of the suction catheter, there remains enough cross-sectional area to function as the discharge channel. This second separate tube also lies substantially free of constraints inside the catheter body lumen, so that the bending performance of the catheter is not adversely affected.

The catheter 1 has a tubular basic body 2 with a substantially circular cross-section. At the proximal end, a trifurcated hub 15 has been formed in which several channels to be described later are brought together. At the distal end, an opening 7 has been formed in the basic body 2 which forms a suction inlet connected with the lumen 3.

In the lumen 3, a first separate tubular body 4 has been received which extends from the proximal end to the distal end. In the tubular body 4, an inlet lumen 5 has been defined which comprises a U-shaped section in the distal end which terminates in a jet nozzle 6.

The proximal hub 40 includes an inlet port 43 with a luer-lock seal 47, a discharge port 42 having a luer-lock seal 46, and a guidewire port 44 which has a hemostatic valve 45. As a result, no separate provision for hemostasis is required so that a manageable unit is obtained.

Hub 40 preferably incorporates a flow directing member 5 adapted to split the pressurized fluid from the inlet port 43. A portion of this fluid is directed into the pressure tube 4, while the remainder of the fluid is directed proximally into the discharge port 42, which encourages the discharge fluid to flow through the discharge lumen 3.

Preferably, the integrated nozzle 6 forms a liquid jet pump. As a result, the suction action at the suction inlet 7 in the distal end of the catheter will be reinforced. Even when the basic body 2 has a very small diameter, sufficient suction can be created without the need for an additional suction pump connected directly to the discharge lumen.

The trifurcated hub 15 comprises a first branch 17 which forms an inlet for the inlet lumen 5. Inside this branch 17, a tube section 20 has been fixed which is connected to a source of liquid under pressure.

A second branch 18 of the trifurcated hub 15 forms the connection with the lumen 3 and functions as the discharge lumen of the catheter. A tube section 25 is connected with the branch 18, and can be connected to a collecting reservoir.

The third branch 19 is also connected with a tube section 32 and forms a connection with a second separate tubular body 30 inside the lumen 3. This tubular body 30 forms a lumen for a guidewire 33. The tubular body 30 has been fed through as far as the distal end of the catheter 1 and has been received with its circumference sealed in the rounded front wall of the distal end. Thus, the guidewire 33 can extend over the entire length through the catheter and be pushed out of the front of the catheter at the opening 31, such that the distal end of guidewire 33 extends distally of the catheter. The catheter can thus be passed over the guidewire 33.

As can be seen clearly, a branch 21 of the pressure connection 20 has been received in the trifurcated hub 15. This branch 21 discharges into the discharge channel 24 with a spray nozzle 22 which is directed in the proximal direction. The liquid under pressure supplied via the pressure line 20 flows partly through the branch 21 and forms a liquid jet, indicated with arrow 23. Thus, a liquid jet pump is formed in the discharge lumen 24, which creates additional suction in the lumen 24. Even in the case of a small diameter for the basic body 2, and hence a relatively small cross section of the area of the lumen 3 available for the discharge channel, sufficient suction can be created at the opening 7.

As the tubes 4 and 30 are different members which have been received substantially free in the basic body 2, they have limited influence on the bending performance of the basic body. Because of the symmetrical cross section of the basic body 2, there is no preferred direction as far as bending is concerned, so that the basic body is not sensitive to buckling.

In operation, the liquid pump supplies pressurized fluid to the inlet port, which passes through the pressure tube and the return tube. The pressure tube directs fluid through the spray nozzle to create the desired suction force at the suction inlet. The suction inlet draws fluid from the body vessel into the discharge lumen and out through the discharge port and the discharge tube into the discharge container.

The catheter, according to the invention, can be manufactured in such a way that the basic body 2 will be made up of a relatively stiff proximal section and a relatively flexible distal section. Manufacturing such a catheter is relatively simple, as the tubular bodies 30 and 4 do not need to be interrupted. Only one joint needs to be made between the two tubular sections making up the basic body 2. A catheter manufactured in this way has consequently a more pliable distal end section, and as a result, more tortuous blood vessels can be reached.

Just like trifurcated hub 15, trifurcated hub 40 has been attached by means of injection molding to the basic body 2 in which the tube-like bodies 4 and 30 have already been received.

The basic body 2 made up of the tubular bodies 4 and 30 is placed in a suitably shaped mold, and the protruding tube sections 4 and 30 are placed in the desired position. The required spaces, in particular those for forming the channel sections, are kept open by means of core pins which connect to the tube-like bodies and the basic body. A tube section 41 is also received in the mold and thus embedded in the trifurcation 40. This tube section 41 has the same function as the branch 21 in FIG. 1.

Figure 2:
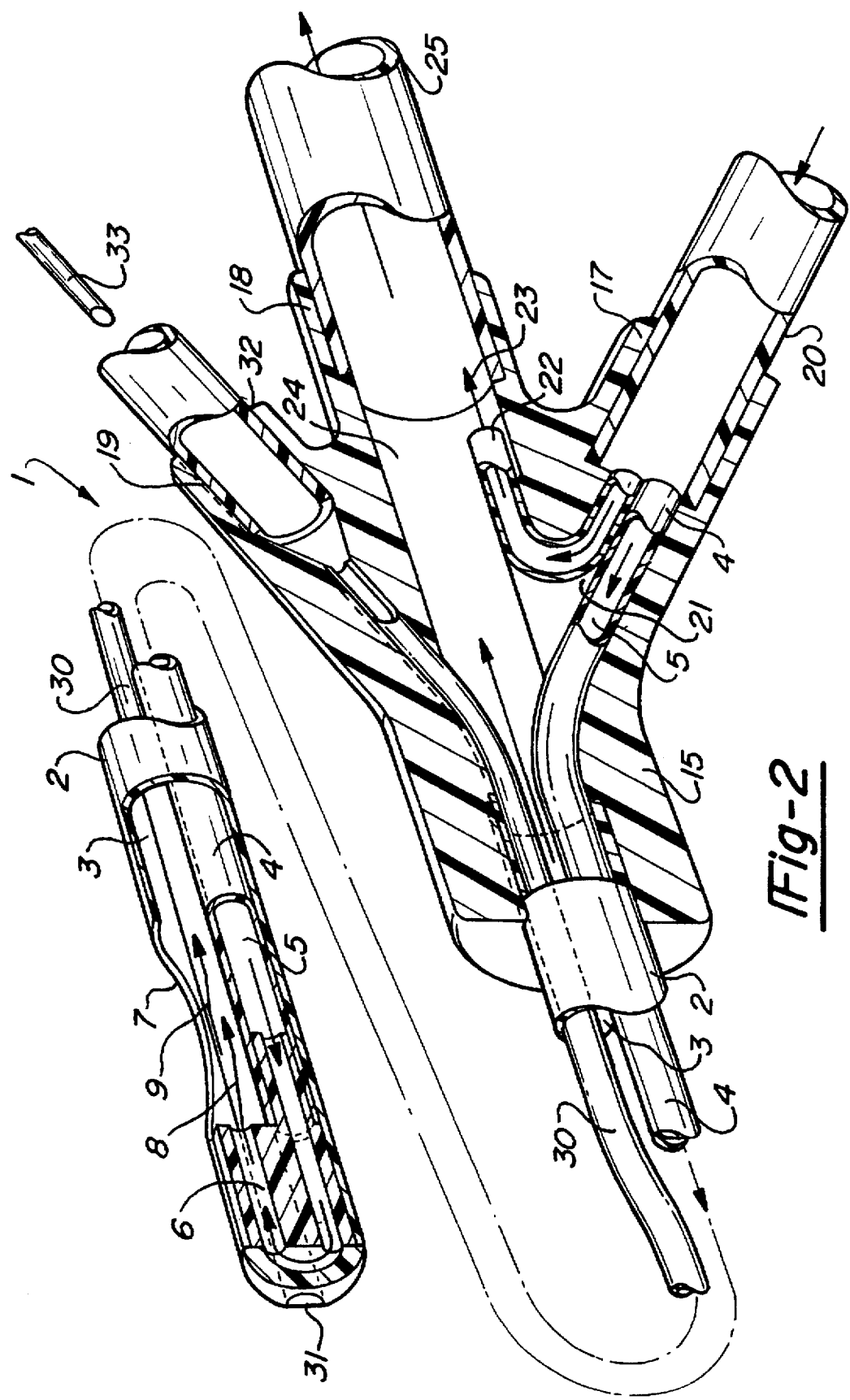
FIG. 2 is a perspective cross-sectional view of a catheter according to the present invention.
Figure 3:
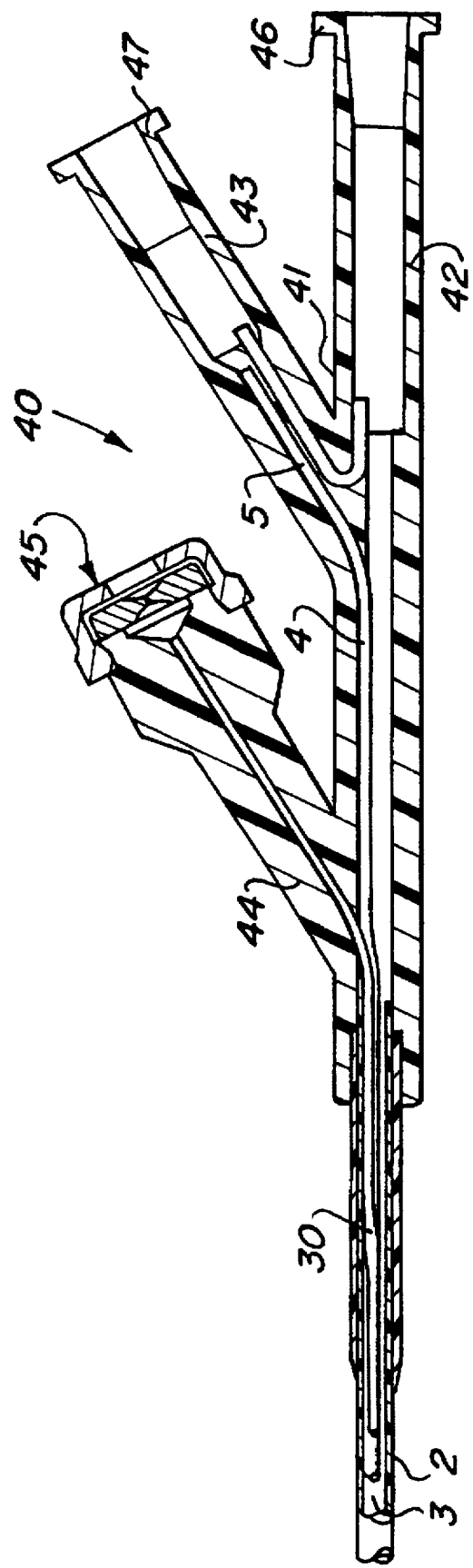
FIG. 3 is a partial cross-sectional view of the proximal portion of a catheter according to the present invention.

As FIG. 2 shows, the three-way trifurcation 40 has been manufactured in such a way that the discharge channel extends in a straight line to a branch 42. The pressure lumen 5 and the guidewire lumen in the tubular body 30 are received in the branches 43 and 44 of the trifurcated hub 40 respectively which extends laterally, parallel to each other at an acute angle, away from the discharge channel.

The branch 44 in which the tubular body 30 has been received is provided with a hemostatic valve 45 at its free end. In this way, a guidewire can be introduced and removed directly through the branch 44 of the trifurcation without a need for any additional hemostatic provisions.

The branch 42 of the discharge lumen and the branch 43 of the pressure lumen are both provided with male luer-lock adapters 46 and 47, respectively. Consequently, the suction catheter according to the invention provided with the trifurcation 40, has a very compact construction and is easy to handle.

Because the pressure lumen 4, and if desired, the guidewire channel 30 have been formed in separate tube-like bodies, it is not difficult to assemble the basic body from a relatively stiff proximal portion and a relatively pliant distal portion. The catheter is therefore easier to manufacture. Thus, a catheter can be made which is capable of reaching more tortuous blood vessels.

It should be understood that an unlimited number of configurations for the present invention can be realized. The foregoing discussion describes merely exemplary embodiments of the principles of the present invention. Those skilled in the art will readily recognize from the description, claims, and drawings that numerous changes and modifications can be made without departing from the spirit and scope of the invention.

We claim:

1. A suction catheter for removing a substance from a body vessel, comprising:
   an elongated catheter tube having a proximal end, a distal end, and a defining a catheter lumen extending between said proximal and distal ends;
   a separate pressure tube received within said catheter lumen and a portion of said catheter lumen defining a discharge lumen, said pressure tube being coupled in fluid communication with a nozzle, and said discharge lumen being coupled in fluid communication with a suction inlet, the nozzle and suction inlet being disposed proximate to said distal end of said catheter body, and
   a separate guidewire tube received within said catheter lumen and defining a guidewire lumen adapted to slidingly accept a guidewire, the guidewire tube being out of fluid communication with said pressure tube;
   wherein said pressure tube is adapted to direct a pressurized fluid through said nozzle, said pressurized fluid tending to cause said pressure tube to bend slightly when flowing through said pressure tube, and wherein said suction inlet and discharge lumen are adapted to allow said substance to enter said suction inlet flow through said discharge lumen, thereby removing said substance from said body vessel, said catheter lumen being larger than the combined cross-sectional areas of said pressure tube and said guidewire tube, and wherein said catheter lumen is sufficiently larger that a portion of said separate pressure tube is free to adjust slightly within the catheter lumen, such that the catheter body tends not to bend when the pressurized fluid flows through the pressure tube.

2. The suction catheter as set forth in claim 1, wherein said guidewire lumen has a distal opening disposed at the distal end of the catheter body, adapted to allow said guidewire to extend distally beyond the distal end of the catheter.

3. The suction catheter as set forth in claim 1, said nozzle is directed in a proximal direction toward said discharge lumen.

4. The suction catheter as set forth in claim 1, further comprising a pressure inlet disposed at a proximal end of said pressure tube, said pressure inlet having a coupling adapted to be coupled with a source of pressurized fluid which flows through said pressure tube and said nozzle, thereby creating a suction force disposed at the suction inlet tending to draw said substance into the suction inlet and through the discharge lumen.

5. The suction catheter as set forth in claim 1, further comprising a discharge outlet disposed at a proximal end of the discharge lumen, said discharge outlet having a coupling adapted to be coupled with a discharge container for receiving said substance from the discharge lumen.

6. The suction catheter as set forth in claim 1, further comprising a hub disposed at the proximal end of the catheter body, said hub having a pressure port coupled with a proximal end of the pressure tube, a discharge port coupled with a proximal end of the discharge lumen, and a guidewire port coupled with the guidewire lumen.

7. The suction catheter as set forth in claim 6, further comprising a hemostatic valve disposed at said guidewire port for preventing body fluids from escaping said guidewire lumen.

8. The suction catheter as set forth in claim 6, wherein said pressure port and said discharge port are provided with luer-lock seals adapted to be coupled with a source of pressurized fluid and a discharge container, respectively.

9. The suction catheter as set forth in claim 1, wherein said catheter body is formed with a relatively stiff proximal portion and a relatively flexible distal portion, thereby enabling the distal end of the catheter body to access more tortuous body vessels.

10. The catheter as set forth in claim 9, wherein said separate pressure tube is formed as an integral, unitary tube having a substantially constant stiffness.

11. A suction catheter for removing a substance from a body vessel, comprising:
   an elongated catheter body having a proximal end, a distal end, and a catheter lumen extending between said proximal and distal ends;
   a separate pressure tube received within said catheter lumen and a discharge lumen formed in said catheter body, said pressure tube being coupled with a nozzle and said discharge lumen being coupled with a suction inlet, the nozzle and suction inlet being disposed proximate to said distal end of said catheter body;
   wherein said pressure tube is adapted to direct a pressurized fluid through said nozzle, and said suction inlet and discharge lumen are adapted to allow said substance to enter said suction inlet and flow through said discharge lumen, thereby removing said substance from said body vessel, said pressurized fluid tending to cause said pressure tube to bend slightly when flowing through said pressure tube, said catheter lumen being larger than the cross-sectional area of said pressure tube, wherein said catheter lumen is sufficiently large that a portion of said separate pressure tube is free to adjust slightly in a radial direction within the catheter lumen, and wherein said separate pressure tube is of sufficient size to allow said pressure tube to move in said radial direction, such that the catheter body tends not to bend when the pressurized fluid flows through the pressure tube,
   a hub disposed at the proximal end of the catheter body, said hub having a pressure port coupled with a proximal end of the pressure tube, a discharge port coupled with a proximal end of the discharge lumen, and a guidewire port coupled with the guidewire lumen,
   wherein said pressure port has coupled adapted to be coupled with a source of pressurized fluid and said discharge port is adapted to be coupled to a discharge container, said hub having a flow directing member adapted to split a pressurized fluid flowing from said source, and to direct a first portion of said pressurized fluid to flow into said pressure tube and to direct a remainder of said pressurized fluid to flow into said discharge port, thereby encouraging said substance to flow from said discharge lumen into the discharge container.

12. A suction catheter for removing a substance from a body vessel, comprising:
   an elongated catheter body having a proximal end and a distal end;
   a pressure lumen and a discharge lumen formed within said catheter body, said pressure lumen being coupled with a nozzle and said discharge lumen being coupled with a suction inlet, the nozzle and suction inlet being disposed proximate to the distal end of the catheter body;
   wherein said pressure lumen is adapted to direct a pressurized fluid through said nozzle, and said suction inlet and discharge lumen are adapted to allow said substance to enter said suction inlet and flow through said discharge lumen, thereby removing said substance from said body vessel;
   a guidewire lumen formed within said catheter body, said guidewire lumen being adapted to receive a guidewire; and
   a hub disposed at the proximal end of the catheter body, said hub having a pressure port coupled with a proximal end of the pressure lumen, a discharge port coupled with a proximal end of the discharge lumen, and a guidewire port coupled with the guidewire lumen;
   wherein said pressure port is adapted to be coupled with a source of pressurized fluid, and said discharge port is adapted to be coupled to a discharge container, said hub further comprising a flow directing member adapted to split a pressurized fluid flowing from said source, and to direct a first portion of said pressurized fluid to flow into said pressure lumen and to direct a remainder of said pressurized fluid flow into said discharge port, thereby encouraging said substance to flow from said discharge lumen into the discharge container.

13. A method of treating a portion of a patient's body vessel, comprising the steps:
   providing a suction catheter and a guidewire, each having a proximal end a distal end, said catheter having a suction inlet disposed near said distal end of said catheter and having a discharge lumen coupled with said suction inlet, said catheter having an elongated catheter tube defining a catheter lumen extending between said proximal and distal ends, a separate pressure tube receive within said catheter lumen, a portion of said catheter lumen defining a discharge lumen, said pressure tube being coupled in fluid communication with a nozzle, and said discharge lumen being coupled in fluid communication with a suction inlet, the nozzle and suction inlet being disposed proximate to said distal end of said catheter body; and a separate guidewire tube received within said catheter lumen and defining a guidewire lumen adapted to slidingly accept a guidewire, the guidewire tube being out of fluid communication with said pressure tube, said catheter lumen being larger than the combined cross-sectional areas of said pressure tube and said guidewire tube, wherein said catheter lumen is sufficiently large that a portion of said separate pressure tube is free to adjust slightly within the catheter lumen; inserting said guidewire within said catheter until said distal end of said guidewire extends distally beyond said distal end of said catheter;

manipulating the guidewire and the catheter to direct them through the desired body vessels until said distal end of said catheter is disposed at the portion of the body vessel to be treated;

injecting a pressurized fluid through said pressure tube and said nozzle, thereby causing said pressure tube to bend slightly within said catheter lumen, and creating a suction force at said suction inlet, thereby causing a substance from said body vessel to enter said suction inlet and flow through said discharge lumen, such that the catheter body tends not to bend when the pressurized fluid flows through the pressure tube; and directing said substance proximally through said discharge lumen, thereby removing said pg.21 substance from said body vessel.

\* \* \* \* \*